United States Patent
List et al.

(10) Patent No.: US 8,263,019 B2
(45) Date of Patent: Sep. 11, 2012

(54) ANALYSIS DEVICE WITH EXCHANGEABLE TEST ELEMENT MAGAZINE

(75) Inventors: Hans List, Hesseneck-Kailbach (DE); Stephan-Michael Frey, Griesheim (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 955 days.

(21) Appl. No.: 12/054,840

(22) Filed: Mar. 25, 2008

(65) Prior Publication Data
US 2008/0267822 A1   Oct. 30, 2008

(30) Foreign Application Priority Data

Mar. 27, 2007   (EP) .................................. 07104960

(51) Int. Cl.
*G01N 33/52* (2006.01)
*G01N 33/48* (2006.01)

(52) U.S. Cl. ........ 422/401; 422/500; 422/419; 422/430; 436/518; 436/125; 221/232; 221/268; 221/270; 606/181; 606/182

(58) Field of Classification Search .................. 422/430, 422/401; 606/181, 182
See application file for complete search history.

(56) References Cited

U.S. PATENT DOCUMENTS

| | | |
|---|---|---|
| 4,911,344 A | 3/1990 | Kahler |
| 5,286,362 A | 2/1994 | Hoenes et al. |
| 5,505,308 A | 4/1996 | Eikmeier et al. |
| 6,159,424 A | 12/2000 | Kauhaniemi et al. |
| 6,827,899 B2 | 12/2004 | Maisey et al. |
| 6,908,008 B2 | 6/2005 | Pugh |
| 7,262,061 B2 | 8/2007 | Petrich et al. |
| 7,582,262 B2 * | 9/2009 | Funke et al. .................. 422/430 |
| 2002/0052618 A1 * | 5/2002 | Haar et al. ..................... 606/181 |
| 2002/0170823 A1 | 11/2002 | Housefield et al. |
| 2003/0089730 A1 | 5/2003 | May et al. |
| 2003/0116583 A1 | 6/2003 | Pugh |
| 2003/0175155 A1 * | 9/2003 | Charlton ......................... 422/61 |
| 2004/0034318 A1 | 2/2004 | Fritz et al. |

FOREIGN PATENT DOCUMENTS

| | | |
|---|---|---|
| EP | 0640393 B1 | 3/1995 |
| EP | 1203563 A2 | 5/2002 |
| EP | 1333756 B1 | 8/2003 |
| EP | 1488736 A1 | 12/2004 |
| WO | 01/48461 A1 | 7/2001 |
| WO | 03/082091 A2 | 10/2003 |
| WO | 03/086103 A2 | 10/2003 |
| WO | 2006/047135 A1 | 5/2006 |
| WO | 2006/076721 A2 | 7/2006 |

* cited by examiner

*Primary Examiner* — Sally Merkling
(74) *Attorney, Agent, or Firm* — Krieg DeVault LLP

(57) ABSTRACT

A measurement system is provided which comprises an analysis device with at least one of a measurement function and a sample collection function, and also at least one magazine configured to receive at least one consumer element therein. The magazine comprises a magazine housing having a pair of openings. The magazine is designed as an exchangeable magazine that can be selectively operatively connected to the analysis device. The analysis device further comprises a closure mechanism having at least one sealing element which is designed to convey at least one consumer element from one of the openings. The sealing element is further configured to sealingly close the openings of the magazine when the sealing element is disposed therein.

38 Claims, 7 Drawing Sheets

ANALYSIS DEVICE WITH EXCHANGEABLE TEST ELEMENT MAGAZINE

CLAIM OF PRIORITY

This application is related to and claims the priority benefit of European Patent Application No. 07 104 960.5, filed on Mar. 27, 2007, the disclosure of which is hereby incorporated by reference herein in its entirety.

TECHNICAL FIELD OF THE INVENTION

The invention relates to a measurement system having an analysis device and a magazine operatively connected to the analysis device and configured to receive at least one consumer element. Such measurement systems and analysis devices are used, for example, for analyzing liquid samples for at least one analyte contained therein. Alternatively, such measurement systems are also used, for example, as lancet systems with a large number of exchangeable disposable lancets. Measurement systems of this kind are used in particular in the field of medicine, for example for monitoring blood glucose, or in the field of chemical analysis, biological analysis or environmental analysis.

BACKGROUND OF THE INVENTION

The monitoring of blood glucose concentrations is an essential part of the daily routine of diabetics. The blood glucose concentration generally has to be determined quickly and reliably several times a day in order, if appropriate, to be able to take suitable medical measures. So as not to restrict the diabetic's daily routine any more than is necessary, suitable portable devices are often employed which are intended to be easy to carry around and to operate, such that the blood glucose concentration can be measured, for example, at the workplace or during leisure time.

Various portable devices are presently available on the market, some of them functioning according to different measurement methods. Various diagnostic methods are used in these devices, for example optical or electrochemical measurement methods. For this purpose, it is possible, for example, to use test elements, for example test strips, onto which a suitable sample is applied. An example of such test strips (in this case an electrochemical test strip) is set forth in U.S. Pat. No. 5,286,362, the disclosure of which is hereby incorporated herein by reference in its entirety. Examples of optical measurement systems are described in document WO 01/48461.

Consumer elements, for example disposable test elements (in particular test strips) thus represent an important element of such measurement systems, in particular of the portable measurement systems. Typically, about 5 to 7 test elements are needed each day by a diabetic. It is essential that the test strips are kept clean and dry, in order to ensure that the measurement of the blood glucose concentration is not rendered inaccurate by contamination or by the action of moisture. The same also applies, for example, to disposable lancets as consumer elements, which also have to be stored in particular in a sterile state.

For this purpose, the consumer elements are usually stored in suitable containers, in order subsequently to be removed from the container by the user and inserted into a suitable analysis device for measurement. Such systems are known from US 2002/0170823 A1, for example, the disclosure of which is hereby incorporated herein by reference in its entirety. In some cases, magazine systems are also used to store and dispense the test strips. Examples of such systems are known from US 2003/0116583 A1, U.S. Pat. No. 6,908,008 B2, EP-0 640 393 B1 and U.S. Pat. No. 4,911,344, the disclosures of which are hereby incorporated herein by reference in their entireties. In these systems, several test strips are stored in a magazine. Moreover, EP 1 488 736 A1, the disclosure of which is hereby incorporated herein by reference in its entirety, describes a system which, instead of having individual test strips, contains a tape made up of one long test strip with a plurality of test fields.

In addition to measurement systems in which magazine and analysis devices are provided as separate units, integrated systems also exist in which several test strips are not only stored in a magazine, but also at the same time afford the possibility of evaluation of these test strips. Examples of integrated systems of this kind are disclosed in U.S. Pat. No. 6,827,899 B2 or in U.S. Pat. No. 6,159,424, the disclosures of which are hereby incorporated herein by reference in their entireties.

There are various forms of test element storage in which protection from external influences is provided either by the magazine itself or by the analysis device. In the former case, the magazine itself must have all the means needed for sealing and afford the possibility of opening the seal, and this results in relatively complex and therefore expensive magazines. An example of such a system is the tape cassette system described in EP 1 488 736 A1, or also systems with sealed films.

In the second case described, in which the sealing is afforded by the analysis device, the analysis device needs to have a sealed chamber that has to be able to be opened by the user when changing the magazine and to be closed again in a sealed manner. U.S. Pat. No. 6,827,899 B2 discloses an example of such a system. A disadvantage of such systems, however, is either that they are technically very complicated or that they have a relatively large seal, which is easily accessed by the user and whose function can therefore be impaired by incorrect use or by inadequate care or cleanliness. Moreover, many of the stated sealing principles, including the principle described in U.S. Pat. No. 6,827,899 B2 for example, do not permit exchange of a magazine, with the result that, after the test elements have been used up, the entire system has to be replaced.

In view of the foregoing, an object of the present invention is therefore to provide a measurement system that at least largely avoids the above-described disadvantages of the prior art. In particular, embodiments of a measurement system according to the present invention are intended to include, in addition to an analysis device, at least one magazine that is exchangeable and that can be easily and quickly connected to the analysis device in a sealed manner.

SUMMARY

This object and others that will be apparent to a person of ordinary skill in the art in view of this disclosure are generally achieved by a measurement system with the features of independent claim 1. Advantageous developments, which can be realized singly or in combination, are set forth in the dependent claims.

In one embodiment, a measurement system is provided which is configured to perform at least one function corresponding to the devices described above. For example, it can be a measurement system for analyzing blood or other body fluids for one or more analytes, for example blood glucose. Alternatively, or in addition, a measurement system according to the present invention can also comprise a sample collection system that has at least one sample collection function, for example the provision of a droplet of blood by perforating an area of skin of a patient. The term "measurement system" is to this extent to be understood in a broad sense.

In other embodiments, the measurement system comprises an analysis device configured to perform one or both of a measurement function and a sample collection function. A measurement function can, for example, include the analysis of a liquid sample by means of a test element. A sample collection function can, for example, include the described perforation of an area of skin by means of a puncturing element, for example a lancet. The term "analysis device" is to this extent to be understood in a broad sense.

In yet other embodiments, the measurement system comprises at least one magazine containing or receiving at least one consumer element, such as a disposable element. The consumer elements are provided according to the function of the analysis device and can therefore include disposable test elements, in particular test strips (for example optical and/or electrochemical test strips, for example according to the prior art described in the introduction). Alternatively, or in additions the consumer elements can include puncturing aids, for example lancets, in particular disposable lancets (for example disposable lancets of the kind described in EP 1 203 563 A2 and/or in EP 1 333 756 B1, the disclosures of which are hereby incorporated by reference herein in their entireties).

Typically, a magazine comprises a magazine housing, which provides at least substantial protection of the consumer elements from environmental influences, in particular from contamination and/or moisture. The magazine housing has at least one opening, said at least one opening permitting the removal and/or dispensing of consumer elements from the housing. The measurement system further comprises a closure mechanism with at least one sealing element (hereinafter also called the sealing element on the device side) in order to close the opening in the housing.

In one embodiment, the magazine is designed as an exchangeable magazine that is operatively connected to the analysis device. For this purpose, the analysis device and/or the magazine can in particular comprise corresponding connection elements, for example bayonet catches, hooks, latches or other types of locking elements. Typically, the analysis device comprises a magazine receiver, in particular a magazine shaft or a magazine compartment, which is configured to receive the magazine and correspondingly connect it operatively to the analysis device.

Measurement systems of this kind correspond, for example, to the measurement system described in U.S. Pat. No. 6,908,008 B2. In contrast to the construction known from said document, however, the sealing element according to the embodiments of the present invention is designed in such a way that it performs a dual function. On the one hand, the sealing element (or entire closure mechanism) is designed to dispense at least one consumer element from the opening. For example, the sealing element can for this purpose be pushed into a first opening of the magazine, in order then to eject a consumer element from a second opening. In this case, the sealing element can include a slide or ram, for example. Other means of dispensing are also conceivable, however, for example a gripper construction with which the consumer element is pulled out of the opening.

On the other hand, however, the sealing element (or entire closure mechanism) is also designed in such a way that, with the magazine in a closed state, it is received in the at least one opening and interacts with said opening, or with the magazine in the area of the opening, such that this opening is closed. "Closed" is to be understood as meaning that a protection against contamination and air moisture is provided, but one that is not necessarily completely airtight. The rate at which moisture penetrates through the closed opening (taking into account any desiccant accommodated in the magazine) should be set such that the function of the consumer elements is not substantially impaired over a customary storage period (i.e. until an expiry date, or usually a few days to a few weeks). In lancet systems, other requirements in terms of sealing have to be met, since here the sterility is more important than the dryness.

In contrast to the known prior art, the described embodiments of a measurement system thus afford the advantage that, on the one hand, the magazine with the consumer elements is exchangeable, such that, when the magazine is empty, only the magazine need be exchanged, while the actual analysis device can be reused. The actual closure mechanism is provided here in the analysis device, such that complex structural parts of this closure mechanism do not need to be disposed of with the magazine, but instead can remain as reusable structural parts in the analysis device. Considerable savings can be made in this way. The operating costs of these systems, which can be designed in particular as portable, light and inexpensive measurement systems, can be reduced to a minimum. At the same time, defects and operating errors can be avoided by the fact that the closure mechanism can be arranged internally in a housing of the analysis device (for example in the interior of a magazine shaft or magazine receiver), typically inaccessible to a user.

According to one embodiment of the present invention, the sealing element and the at least one opening thus interact, in the closed state of the measurement system, in order to seal off the at least one opening. This interaction can take place in various ways. For example, the opening or the magazine in the area of the opening and/or the sealing element can each have sealing surfaces which are pressed against one another in the closed state, in order in this way to achieve a sealing action. Alternatively, or in addition, the sealing element and/or the opening, or the magazine in the area of the opening, can also have additional sealing elements, for example elastic sealing elements. For this purpose, the sealing element and/or the opening can be designed to be completely or partially deformable, in particular elastic, in order to achieve the sealing action when suitably pressed onto each other. A combination of the techniques is also possible, for example the combination of a smooth sealing surface and a deformable sealing element, in which case the allocation of these elements to the sealing element and to the opening can be chosen in any desired way.

In one embodiment, the sealing element has a sealing surface, such as a smooth sealing surface. As the mating component, the opening can then have one or more deformable seals provide on the magazine, which seals interact with the sealing surface. For example, the opening can have at least one sealing gap, in particular a sealing lip. Here, a "sealing lip" is to be understood, for example, as a rubber seal which extends around the periphery or interior of an opening and into which the sealing element can be pushed.

Other embodiments concern the sealing element itself. Thus, for example, in order to improve the sealing action, it has proven useful if the sealing element, in a direction of insertion into the opening (that is to say in the direction in which the sealing element is pushed by the closure mechanism into the opening) has a narrowing cross section at least in part (that is to say, for example, in a portion of the sealing element). In this way, the force exerted by the closure mechanism can provide a force component via which the sealing element is sealingly pressed against the wall of the opening.

The sealing element can be designed in such a way that it is formed for example in some areas with a constant cross section and in other areas, by contrast, with the described narrowing cross section (for example a conical cross section). In this way, for example, the first portion provided with a constant cross section can be used to dispense or push out a consumer element, in order thereafter, in one and the same movement, to insert the conical portion into the opening and thereby close the opening.

The closure mechanism can in particular be designed in such a way that the sealing element conveys a consumer element out of the magazine and into a use position. In this use position, for example, the concentration of an analyte in a liquid sample can be determined by means of the consumer element designed as test strip. Alternatively, or in addition, a consumer element designed as a lancet can be employed to perforate an area of skin in the use position, in order to produce a droplet of blood. Other types of uses are also conceivable, however.

If the consumer element is conveyed by means of the sealing element out of the magazine into a use position, then in other embodiments the sealing element can also perform other tasks. For example, the sealing element can also serve to convey the consumer element from the use position to a disposal position and/or to a disposal unit after use. For this purpose, for example, in one embodiment the measurement system can comprise a waste container that is able to receive consumer elements that have been used in this way. This waste container can be designed, for example, such that it is connected releasably to the measurement system and/or analysis device, in order to allow regular emptying. In other embodiments, alternatively, or in addition, the waste container can also be a component part of the magazine. Instead of a waste container, in yet other embodiments, it is also possible for used consumer elements to be discarded directly. Various embodiments of this are conceivable.

In addition to the above-described functions of dispensing a consumer element and of sealing the opening, the sealing element can also perform other tasks and functions. These functions can, for example, be associated with dispensing the consumer element, such that, for example, the sealing element can include grippers, slides or the like (see also above). Alternatively, or in addition, the sealing element can also perform other electrical, optical or mechanical functions, which can be adapted to the nature and mode of operation of the consumer element.

For example, in one embodiment the sealing element can have a jacket with at least one sealing surface for sealing off the opening, and, in the interior of the sealing element, an application channel that extends axially in the sealing element. Various functional elements can be received in this application channel, and said application channel can be designed with any desired cross section.

Thus, for example, at least one electrical contact (for example a supply line) for contacting a consumer element can be received in the application channel. In this way, electrochemical test strips can be contacted via the sealing element for example, in order to carry out a corresponding measurement.

Alternatively, or in addition, in other embodiments an optical device can also be received in the application channel. This optical device can, for example, include a light source and/or a light wave guide, for example in order to permit excitation of an optical test strip and/or to gather light emitted from the optical test strip and convey it to a detector device. Other types of optical devices are also conceivable.

In a third alternative or additional possibility, in yet other embodiments a mechanical device can be provided in the at least one application channel. For example, this mechanical device can include a device for handling the consumer elements. One example that may be mentioned here is that of a device that executes a mechanical movement in order to establish electrical contact of test elements. This can be useful, for example, if test elements with very thin contacts are used, which can in this way be contacted gently for example. Another alternative or additional mechanical function that can be incorporated is that of a drive ram or another drive device that can be arranged in the application channel and is used to operate a lancet system. For example, the at least one magazine can accommodate disposable lancets, which are brought by the sealing element into an application position, where the drive ram, for example mounted movably with respect to the rest of the sealing element inside the application channel, drives said lancets in a rapid perforating movement. Other configurations of the sealing element are also conceivable.

BRIEF DESCRIPTION OF THE DRAWINGS

Further details and features of the invention are set forth in the following description of illustrative embodiments in conjunction with the dependent claims. However, the invention is not limited to the illustrative embodiments. The illustrative embodiments are depicted schematically in the figures. Identical reference numbers in the individual figures designate identical elements or designate elements that are of identical function or that correspond to one another in terms of their functions.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
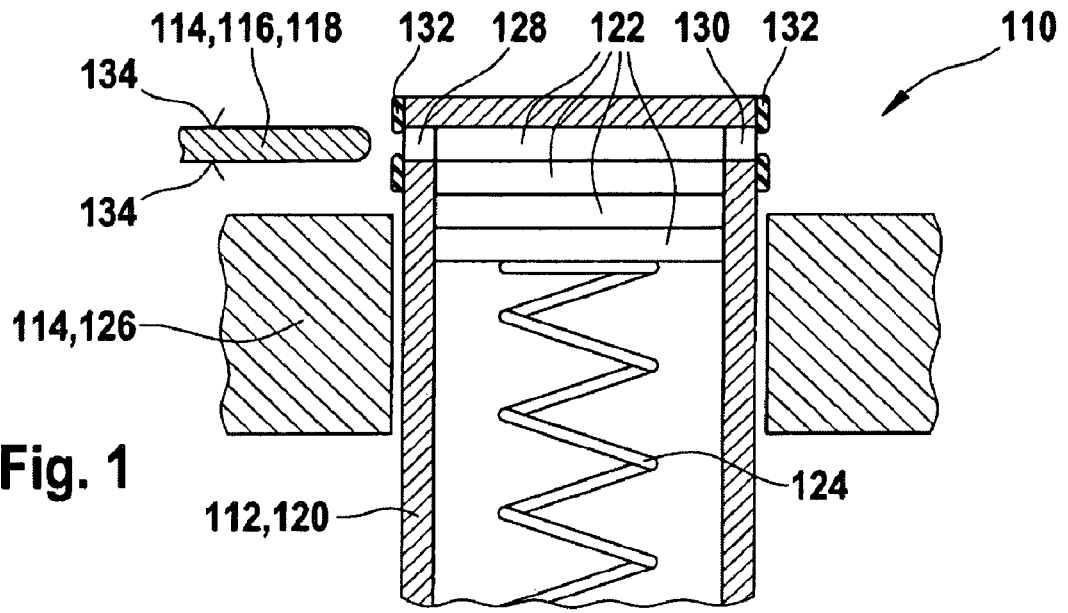
FIG. 1 illustrates a cross sectional view of a measurement system according to one embodiment of the present the invention, comprising a magazine in the opened state.

FIG. 1 shows, in a greatly simplified view, a detail of one embodiment of a measurement system 110 according to the present invention. The measurement system 110 comprises a magazine 112 and an analysis device 114. In this simplified depiction of the analysis device 114, only part of a closure mechanism 116 with a sealing element 118 is shown. For the other functions of the analysis device 114 and for examples of its construction, reference may be made to the description of the other illustrative embodiments (see below).

The magazine 112 has a magazine housing 120. This magazine housing is generally designed as a sealed housing and is configured to receive or otherwise contain a plurality of test elements 122 which are stacked on one another in parallel and which, in this illustrative embodiment, are designed as test strips. Other types of consumer elements are also possible, however.

In the illustrative embodiment shown, the magazine 112 is designed as a bar or straight-line magazine and has a magazine spring 124, which acts with a biasing force on the stack of test elements 122.

The magazine 112 in this embodiment is designed to be pushed into a magazine shaft 126 (only indicated symbolically in FIG. 1) of the analysis device 114. However, other configurations of the connection or reception of the magazine 112 to the analysis device 114 are also conceivable.

The otherwise substantially sealed magazine housing 120 generally has two openings 128, 130 at its upper end. Corresponding to the design of the test elements 122 as test strips, these openings 128, 130, in particular the opening 130 serving as dispensing opening, can be designed as slit openings.

According to the illustrative embodiment in FIG. 1, the magazine 112 also comprises seals 132 on the magazine side, proximate the openings 128, 130. In the illustrative embodiment shown, these seals 132 are designed as sealing lips which surround, e.g., the opening 128 but which, in the opened state, do not lie firmly on each other and narrow the opening 128 only inappreciably. As an alternative to simple sealing lips, other types of circumferential seals can be used, for example sealing rings of suitable configuration, foam seals or like seals, and may be provided about or within the openings 128, 130 for effecting a sealed closing thereof. A simple smooth opening is also conceivable, i.e. a configuration without additional seals on the magazine side, such as shown in the embodiments illustrated in FIGS. 3 and 4.

As a mating piece for these seals 132, the sealing element 118, which is here designed as a simple rod or sealing slide, has sealing surfaces 134 designed as smooth surfaces. For example, the sealing element 118 can be a rod with constant rectangular cross section, and this rectangular cross section for example substantially corresponds to the cross section of the openings 128, 130 or is only inappreciably smaller than these. Alternatively, the cross section can also be chosen slightly larger, such that the sealing element 118 forms a press fit with the openings 128, 130 in the closed state.

Figure 2:
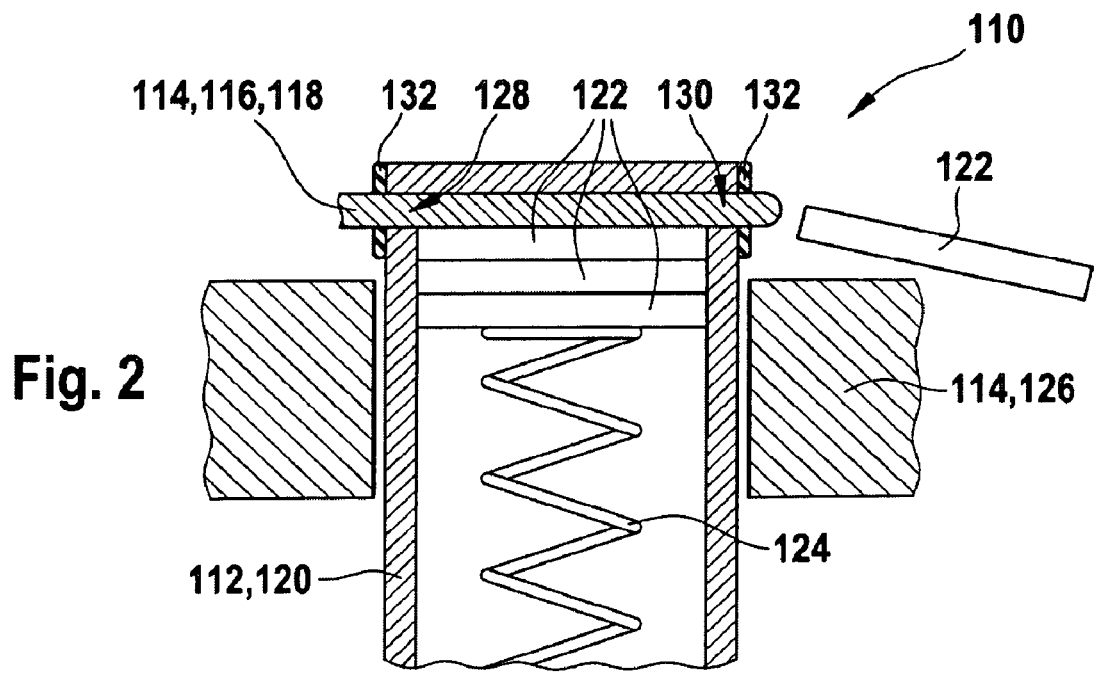
FIG. 2 illustrates the measurement system of FIG. 1 with the magazine in the closed state.

FIGS. 1 and 2 both show different positions of a measurement system 110. FIG. 1 shows an opened position in which the sealing element 118 is pulled out of the openings 128, 130, as a result of which these openings 128, 130 are freed. In this position, for example, the magazine 112 can be exchanged. Moreover, in this position, the uppermost test element 122 can be pushed by the magazine spring 124 and pressed against the inner face of the magazine lid.

FIG. 2 shows how the sealing element 118 on the device side is initially pushed into the left-hand opening 128 by a component (not shown in FIGS. 1 and 2) of the closure mechanism 116, dispenses the uppermost test element 122 from the right-hand opening 130 and then closes the right-hand opening 130. For this closing action, the sealing surfaces 134 (see FIG. 1) interact with the seals 132. After the dispensing action, the sealing element 118 then remains in the closed position shown in FIG. 2. Thus, the openings 128, 130 are open only briefly during the dispensing of a test element 122 (i.e. typically not longer than a few seconds), and are then closed by the sealing element 118 for a longer time, during which the measurement system 110 is not in use.

The seals 132 can be designed as sealing lips, as has been described above, and can have deformable or flexible properties and be made, for example, of rubber or of another plastic. Accordingly, in the closed state shown in FIG. 2, the sealing element 118 generally closes the magazine 112 and thus shields the test elements 122 inside the magazine 112 from contamination and the effects of moisture. The magazine spring 124 presses the uppermost of these test elements 122 against the lower smooth sealing surface 134 of the sealing element 118 on the device side.

In the closed state shown in FIG. 2, the sealing element 118 on the device side also contributes to locking the magazine 112 in the magazine shaft 126. The magazine 112 is in this way securely connected to the analysis device 114. In order also to fix the magazine 112 in the magazine shaft 126 in the opened state shown in FIG. 1 (which generally exists only briefly), additional locking elements can also be provided.

The ejection of one of the test elements 122 by the sealing element 118 on the device side is depicted symbolically in FIG. 2. This depiction is greatly simplified. In the proposed measurement system with the at least one measurement function, this test element 122 can also be forwarded to a measurement function, for example in order to be electrically contacted or to be delivered for other purposes. This is explained in more detail below with reference to other illustrative embodiments.

To be able to deliver a new magazine 112 with unused test elements 122 to the measurement system 110, such a magazine 112 can, in one embodiment, be removed from a primary packaging, for example a blister pack. The openings 128, 130 can additionally or alternatively be sealed by sealing films or other opening fillers (not shown). If films or fillers are provided in the alternative, then clearly it is possible to dispense with the packaging (for example the blister pack).

Before the magazine 112 is pushed into the magazine shaft 126, these sealing films can be removed from the openings 128, 130. In doing so, the interior of the magazine 112 is briefly exposed to the atmosphere. To deal with any incoming moisture, a desiccant can be provided in the interior of the magazine 112, as described above, which desiccant is configured to take up the moisture.

After a magazine 112 has been inserted into a magazine shaft 126 of an analysis device 114, the closure mechanism 116 is actuated, and the sealing element 118 is pushed into the openings 128, 130. The closed state shown in FIG. 2 is the state in which the measurement system 110 is provided when it is not in use. In order to avoid losing the uppermost test element 122 when inserting a fresh magazine 112 for the first time and then locking it by means of the sealing element 118, in one embodiment the uppermost test element 122 in each new magazine 112, is configured as a dummy element, for example in the form of a cheap plastic or cardboard part which is ejected and disposed of at the first time of use. In other embodiments, the uppermost test element 122 may comprise a check strip or code strip configured to provide code information, lot information, or any other information as desired to the measurement system 110.

In one embodiment, the magazines 112 are designed as disposable or reusable magazines. An advantage of this design of the sealing elements 118 and seals 132 is also that the seal formed by these sealing elements 118 and seals 132 can be exchanged with each magazine 112, whereas more costly parts, such as the closure mechanism 116, can remain in the analysis device 114 and can thus be reused.

In the illustrative embodiment of the measurement system 110 shown in FIGS. 1 and 2, the sealing element 118 has a cross section that remains substantially constant in the axial direction. Accordingly, this sealing element 118 interacts with the seals 132. The production of seals 132, however, may increase the costs of the magazine 112. Accordingly, FIGS. 3 and 4 show another illustrative embodiment of a measurement system 110, which corresponds substantially to the illustrative embodiment according to FIGS. 1 and 2.

Figure 3:
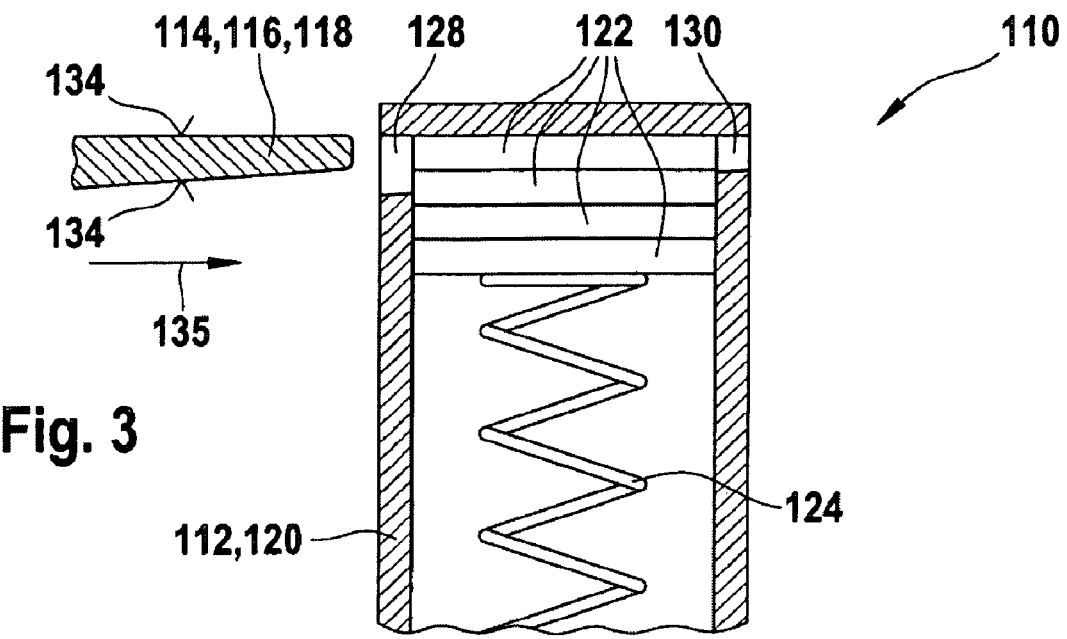
FIG. 3 illustrates an alternative embodiment of a measurement system according to the present invention, comprising a conical sealing element, and the magazine in the opened state.
Figure 4:
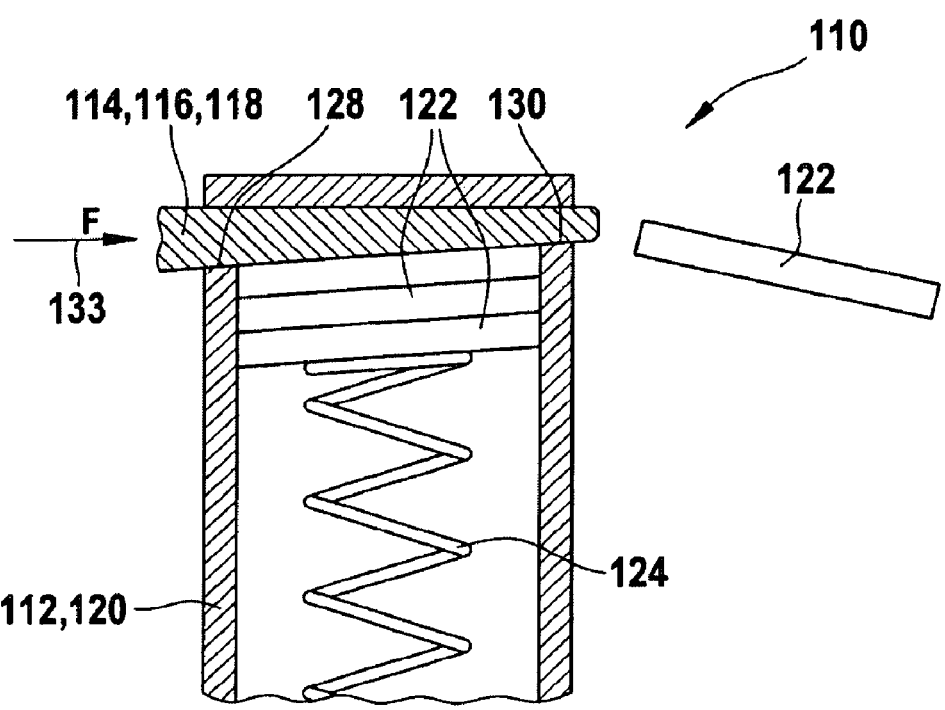
FIG. 4 illustrates the measurement system of FIG. 3 with the magazine in the closed state.

In contrast, however, in the illustrative embodiment according to FIGS. 3 and 4, a "conical" sealing element 118 is provided with the analysis device 114. This conical sealing element 118 is designed in such a way that it narrows in cross section in the direction of insertion (symbolically indicated by the arrow 135 in FIG. 3). For example, in the inserted state, the sealing element can narrow in cross section between the openings 128 and 130 by 10 to 90%, the typical extent of this narrowing being in the range between 30 and 50%. However, it should at all times also be ensured that, even in the opened state according to FIG. 3, the second uppermost consumer element 122, which as shown is at least partially exposed to opening 128, cannot slide out of the opening 128 and is instead configured to be held inside the magazine 112. Accordingly, the opening 128 in one embodiment is smaller than twice the thickness of a consumer element 122 (and therefore also the corresponding cross section of the sealing element 118), such that the second uppermost test element is retained by an edge of the opening 128.

In this embodiment comprising a narrowing or conical design of the sealing element 118, the insertion force, designated symbolically in FIG. 4 by reference number 133, comprises a component perpendicular to the sealing surface 134, such that the sealing element 118 is pressed against the magazine housing 120 in the area of the openings 128, 130. The sealing action is considerably improved by this pressing. Otherwise, the structure and mode of operation of the measurement system 110 according to FIGS. 3 and 4 corresponds substantially to FIGS. 1 and 2.

However, it is not essential for the conical nature of the sealing element 118 to be uniform along the entire length of the sealing element 118. It is also possible for the surface 134 of the sealing element 118 to be designed with different sections along its axial extent. For example, a prismatic part can first of all serve to push the consumer element 122 out of the magazine 112 and onward into an active position. The sealing element 118 would therefore be conical only in a final part of the length of said sealing element 118 and would effectively serve to close the magazine openings 128, 130 (see, for example, the illustrative embodiment below in FIG. 6). In this case, the magazine 112 would likewise be opened for the brief measurement time, but would be closed during the long period of time between two measurements.

A similar design of the sealing element 118 with a non-uniform cross section in the axial direction could also be combined with the illustrative embodiment according to FIGS. 1 and 2, that is to say with the additional seals 132 (for example in the form of elastomer seals). In this case, the sealing slide or sealing element 118 could be thinner in cross section in its front part. Only when the sealing element 118 has been pushed into the magazine 112 completely, that is to say also with its rear part of larger cross section, are the openings 128, 130 closed tight.

Figure 5:
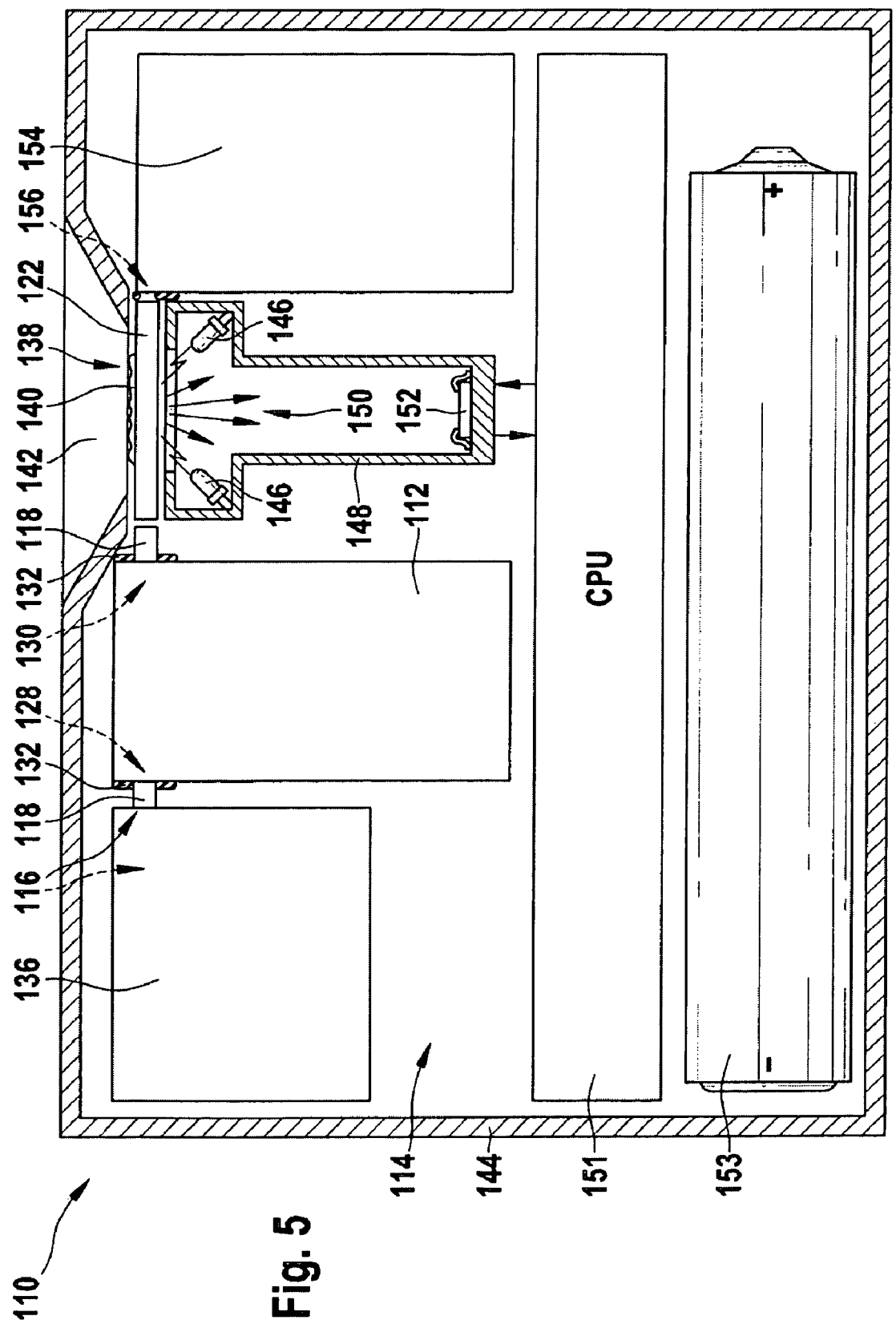
FIG. 5 illustrates an embodiment of a measurement system according to the present invention, comprising an optical detector and a waste container.

Whereas the actual analysis device 114 is only symbolically indicated in each of FIGS. 1 to 4, a more extensive illustration of an embodiment of a measurement system 110 is shown in FIG. 5, comprising analysis device 114 with a magazine 112 received therein. In FIG. 5, the magazine 112 is designed as in the illustrative embodiment according to FIGS. 1 and 2. Nevertheless, FIG. 5 is only a schematic simplified representation of a measurement system 110, and additional elements may also be present, for example additional holding and locking elements for the magazine 112 (for example a magazine shaft 126).

Generally, embodiments of analysis device 114 comprise a closure mechanism 116 which, in addition to the sealing element 118 (which in this case is designed for example as shown in FIG. 1 or 2), has a drive 136 for actuating the sealing element 118. By means of this drive 136, the sealing element 118 can be driven linearly in the direction of insertion 135 (not shown in FIG. 5; see, e.g., FIG. 3) or counter to this direction of insertion 135. In this way, the sealing element 118 can be pushed into the interior of the magazine 112 via the first opening 128, which in this illustrative embodiment is once again designed with the seals 132. In this connection, reference may largely be made to the above description of FIGS. 1 and 2. The drive 136 can include, for example, mechanical drives and/or electromechanical drives of kinds known to a person skilled in the art.

As is shown in FIG. 2 for example, the pushing into the first opening 128 causes a test element 122 to be pushed out of the second opening 130 (likewise equipped with seals 132). In one embodiment, the sealing element 118 pushes it out until the test element 122 is transferred to a measurement position 138 as shown in FIG. 5. In this measurement position 138, a liquid sample 140 (which is only symbolically indicated in FIG. 5) can be applied from outside the system 110 through an application aperture 142 in the housing 144 of the analysis device 114 and onto the test element 122 in the measurement position 138. The application aperture 142 is, for example, designed such that a thumb, with a droplet of blood arranged thereon, can be pressed onto the test element 122 in order to transfer the droplet of blood onto the test element 122.

In the illustrative embodiment in FIG. 5, the test element 122 is an optical test strip, for example. In this optical test strip, the liquid sample 140 (if it contains the analyte) triggers a color-changing reaction, for example when the analyte that is to be detected reacts with a corresponding reagent in the test strip 122.

In an exemplary embodiment for optical detection of an analyte, this color reaction can be detected by means of suitable light-emitting diodes 146 in a detector 148 of the analysis device 114. These light-emitting diodes 146 (other excitation sources can also be used) irradiate the test element 122 with excitation light. This excitation generates a fluorescence in the test element 122, for example, the presence and/or intensity of this fluorescence being dependent on the presence and concentration of the analyte that is to be detected. This fluorescence light, which is designated symbolically in FIG. 5 by reference number 150, is taken up by an optical detector 152 (for example a photodiode). The signals thus generated are transmitted from the optical detector 152 to a control and evaluation unit 151 (designated symbolically in FIG. 5 by "CPU"). These signals can then be used, in the control and evaluation unit 151, to establish the presence or concentration of the analyte that is to be detected in the liquid sample 140.

It should be noted that the detection method described on the basis of the embodiment in FIG. 5 is only to be understood as one example. Instead of fluorescence light, it is also possible, for example, to detect reflected light components, phosphorescence components or other types of light. Additional electrical, mechanical, electromechanical or optical components can also be provided in the analysis device 114 but are not shown in FIG. 5. In the illustrative embodiment according to FIG. 5, the whole analysis device 114 is powered by a battery 153. However, other embodiments are also conceivable, for example a power supply via a cable, a wireless power supply, power supply from other types of energy accumulators, or other types of energy supply.

Instead of having optical test elements 122, the analysis device 114 shown in FIG. 5 can also be designed, alternatively or in addition, in such a way that it can be operated with other types of test elements 122. For example, electrochemical test elements 122 can be used for this purpose. For example, the test element 122 in the measurement position 138 can be contacted by corresponding electrical contacts for this purpose. These contacts can, for example, also be provided on the tip of the sealing element 118.

In one embodiment of the present invention, the sealing element 118 is designed in such a way that it is able not only to transfer the uppermost test element 122 from the interior of the magazine 112 into the measurement, position 138, but also to transfer a used test element 122 from the measurement position 138 to a disposal position. For this purpose, the analysis device 114 can, for example, have an ejection aperture acting as the disposal aperture through which the used test element 122 is ejected from the housing 144 of the analysis device 114. Alternatively or in addition, the analysis device 114, as shown in FIG. 5, can also have a waste container 154 in a disposal position. The waste container 154 has a disposal aperture 156. The length of the sealing element 118 is such that it can push the test element 122 from the measurement position 138 through the disposal aperture 156 and into the interior of the waste container 154. The waste container 154 can then be emptied at regular intervals or as and when required, for example via a flap (not shown in FIG. 5) and/or by the waste container 154 being removed from the housing 144 of the analysis device 114. In this way, used test elements 122 can be disposed of hygienically without risk of infection. In the illustrative embodiment shown in FIG. 5, the sealing element 118 therefore has the threefold function of dispensing a test element 122 from the magazine 112 to the measurement position 138, transferring the test element 122 from the measurement position 138 into the waste container 154, and sealing the magazine 112.

In the illustrative embodiments discussed thus far, the consumer elements 122 comprise test elements that serve to detect the at least one analyte in the at least one sample 140. Alternatively or in addition to these test elements 122, however, the consumer elements can also include other types of consumer elements, for example lancet systems for perforating an area of skin. Measurement systems 110 of this kind are shown by way of example in FIGS. 6 to 9.

Figure 6:
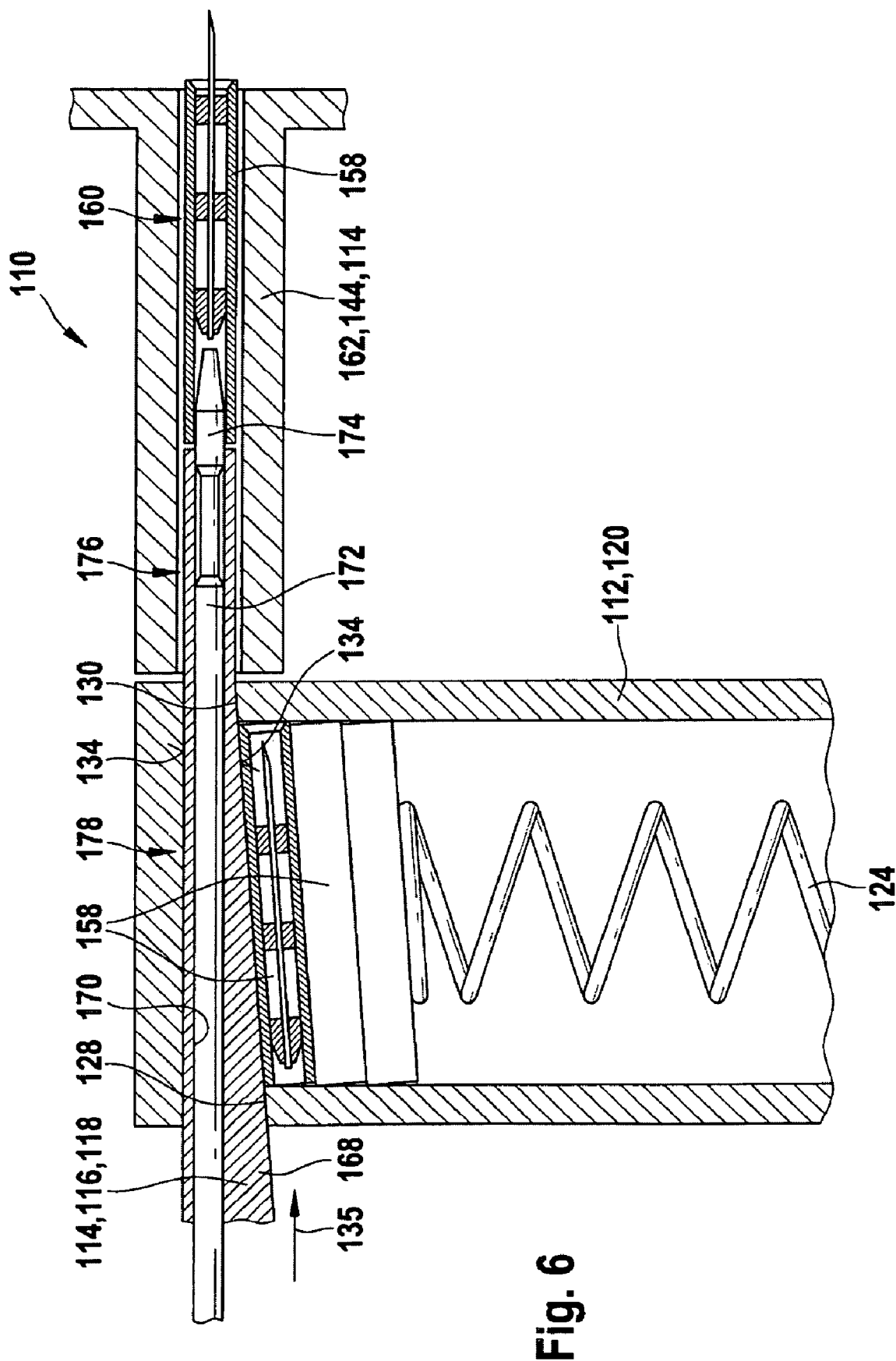
FIG. 6 illustrates a measurement system with a lancet system and a hollow sealing element according to another embodiment of the present invention.

Thus, FIG. 6 shows an embodiment of a measurement system 110 in a similar view and a similar configuration to that in FIG. 4. In this illustrative embodiment, the consumer elements are each lancet systems 158, which are again received in a magazine 112 (again designed as a straight-line or bar magazine) and are acted upon with pressure by a magazine spring 124. Once again, the magazine 112 has two openings 128, 130, and, analogously to FIGS. 3 and 4, the first opening 128 is again larger than the second opening 130. Also analogously to FIGS. 3 and 4, a cone-shaped sealing element 118 can be pushed in a direction of insertion 135 into the interior of the magazine 112. The uppermost lancet system 158 is thus pushed out of the interior of the magazine 112 and pushed into a use position 160. This use position 160 is located in a suitably designed guide structure 162 in the housing 144 of the analysis device 114.

Figure 7:
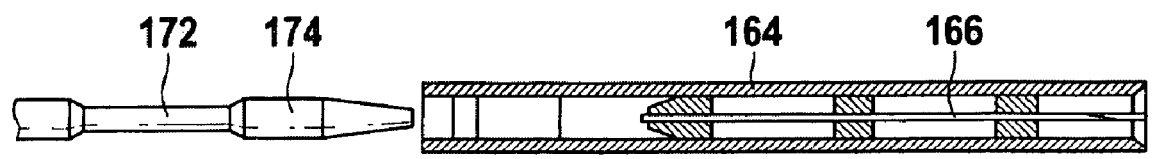
FIGS. 7 and 8 illustrate cross sectional views of examples of interaction between a lancet ram and a lancet system in yet other embodiments according to the present invention.
Figure 8:
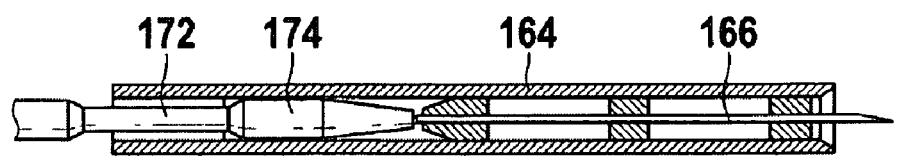
Figure 9:
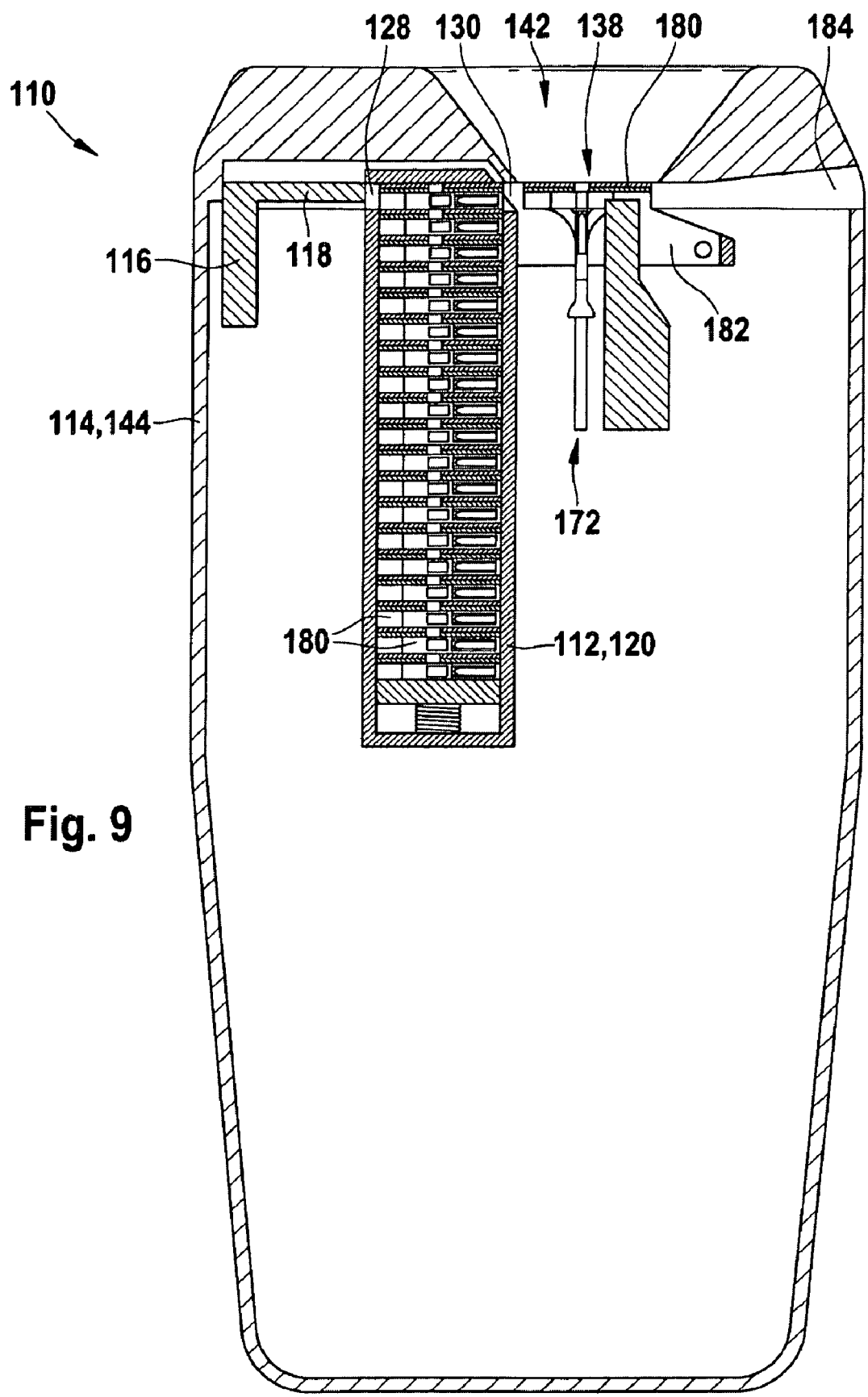
FIG. 9 illustrates an embodiment of a measurement system comprising combined consumer elements.

In this illustrative embodiment, the lancet system 158 is configured as a disposable lancet system and can, for example, correspond to a design of the kind described in EP 1 333 756 B1, the disclosure of which is hereby incorporated herein by reference in its entirety An embodiment of a lancet system 158 is shown in detail in FIGS. 7 and 8. It comprises a lancet housing 164, in which a lancet needle 166 is slidably received.

As can be seen from FIG. 6, the sealing element 118 in this illustrative embodiment comprises a jacket 168 in which an application channel 170 extends parallel to the direction of insertion 135. In this illustrative embodiment, this application channel 170 receives a drive ram 172 mounted slidably in the application channel 170. At its front end 174, this drive ram 172 penetrates into the lancet housing 164. When the drive ram 172 shoots forward, the lancet needle 166 is advanced inside the lancet housing 164 and projects outward, in order to perforate an area of skin. For the further functioning of the lancet systems 158 and for alternative embodiments of the lancet systems 158, reference may be made to aforementioned EP 1 333 756 B1.

Moreover, in the illustrative embodiment shown in FIG. 6, the sealing element 118 is not designed uniformly in all areas. Thus, in its front area 176, the sealing element 118 is prismatic and has a constant cross section. This area is adjoined by a conical area 178 which, as has been described above, is configured for sealing the openings 128, 130. The position shown in FIG. 6 is the closed position in which the magazine 112 is sealed off substantially tightly by the sealing element 118. The drive ram 172 does not have to be received in a sealed manner in the application channel 170, because the jacket 168 is able to close the magazine 112 alone via its outer surface 134.

Again, FIG. 6 does not show the remaining component parts of the analysis device 114. In particular, the closure mechanism 116 is again not shown completely and, as has been described for example in FIG. 5, it can also include a drive 136. In one embodiment, this drive 136 does not only include a linear drive for the sealing element 118, but also a drive unit for the drive ram 172, such that the latter can be moved independently of the sealing element 118 in and counter to the direction of insertion 135.

In the illustrative embodiment according to FIG. 6, the drive ram 172 moves parallel to the direction of insertion 135 of the sealing element 118. However, this is not absolutely essential, as is shown for example in the illustrative embodiment in FIG. 9. This illustrative embodiment of a measurement system 110 is a modification of a measurement system known from EP 1 203 563 A2, the disclosure of which is hereby incorporated herein by reference in its entirety, which uses combined consumer elements 180.

These combined consumer elements are received in a magazine 112, which is again designed for example as a bar or straight-line magazine, analogously to the above illustrative embodiments. The magazine 112 once again has two openings 128, 130. A sealing element 118 can be pushed through the first opening 128 into the interior of the magazine 112, in order to push the uppermost consumer element 180 out of the magazine 112 and into a measurement position 138. The sealing element 118 is once again designed such that, in the closed position, that is to say when the test element is pushed out, it remains in the openings 128, 130 and closes these in a sealed manner. A corresponding drive 136 of the closure mechanism 116 is not shown in FIG. 9.

The combined consumer elements 180 are designed in the manner described in EP 1 203 563 A2 and comprise both a test element and also a lancet system. In the measurement position 138, part of the lancet system folds downwards and can be actuated by means of a drive ram 172. In this actuation, the lancet emerges from the application aperture 142 in a manner perpendicular to the direction of extent of the combined consumer element 180 and in doing so perforates an area of skin of a finger, for example, which is placed onto the application aperture 142. The droplet of blood thus formed is applied directly onto the test element integrated in the combined consumer element 180, in order to be tested there, for example electrochemically or optically. For further details of the combined consumer element 180, reference may be made to the above-mentioned patent publication.

As has been generally described above, the sealing element 118 typically closes both openings 128, 130 in the closed state. The measurement system described in EP 1 203 563 A2 does not have this feature, however. In addition, the system described in EP 1 203 563 A2 has an ejector, which is also provided in the illustrative embodiment in FIG. 9 and is designated there by reference number 182. This ejector serves to eject used consumer elements 180 through an ejection aperture 184. In a development of the illustrative embodiment according to FIG. 9, this ejector 182 is omitted by virtue of the sealing element 118 or closure mechanism 116 being designed such that, analogously to the example according to FIG. 5, these also push the used consumer element 180 through the ejection aperture 184 from the measurement position 138. In this way, the additional mechanical elements of the ejector 182 can be avoided.

Figure 10:
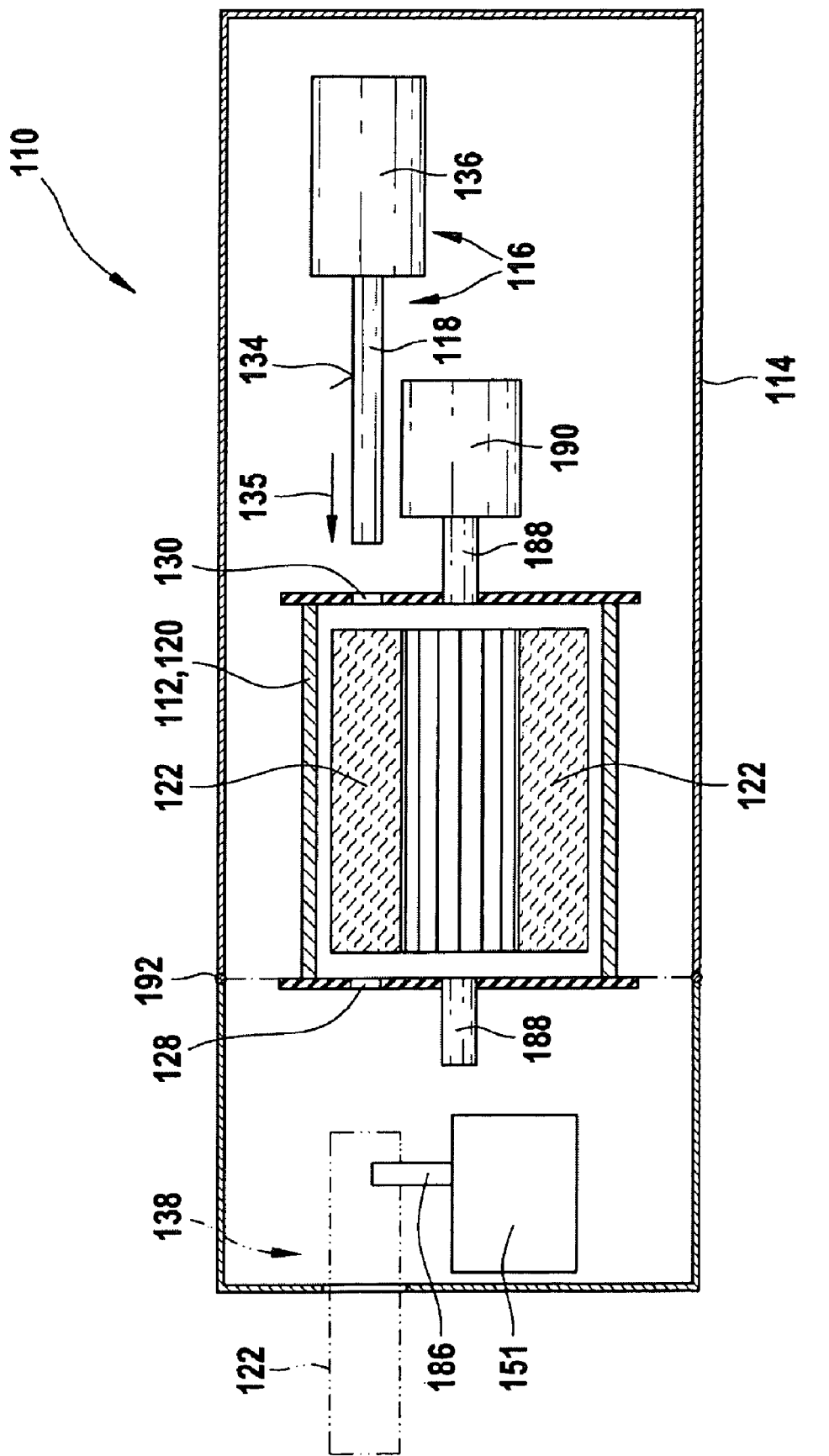
FIG. 10 illustrates an embodiment of a measurement system comprising a drum magazine.

In the illustrative embodiments described up to this point, the magazine 112 is in each case designed and shown as a bar or straight-line magazine. By contrast, FIG. 10 shows an alternative illustrative embodiment of a measurement system 110 in which the magazine 112 is designed as a drum magazine. Once again, this measurement system 110 is only shown schematically.

The measurement system 110 once again comprises an analysis device 114, it again being assumed here for purposes of illustrating an embodiment that this analysis device 114 is a blood glucose meter. The test elements 122 are designed here as electrochemical test strips, for example. For this purpose, the analysis device 114 again has a measurement position 138, in which the test elements 122 can be contacted electrically 186 and can have a liquid sample (not shown) applied to them. The analysis device 114 also comprises a control and evaluation unit 151, which is also shown very schematically in FIG. 10. Further devices can also be provided, for example a microcomputer for evaluation, operating elements, output elements or the like, as may also be the case for example in the illustrative embodiment shown according to FIG. 5 or according to FIG. 9.

In the embodiment according to FIG. 10, a magazine 112 is again provided, but one which, as has been described above, is designed as a drum magazine. In this drum magazine 112, the test elements 122 can be mounted, for example, in a star shape and symmetrically with respect to the drum axle. For this purpose, for example, the interior of the drum magazine 112 can be provided with individual chambers in which the test elements 122 are screened from one another. Alternatively, the interior of the magazine 112 can also be designed as a single large chamber, with all the test elements 122 being mounted in the same chamber atmosphere.

Accordingly, a storage device can also be provided, which is again not shown in FIG. 10. This storage device can interact with corresponding axles 188 by means of which the magazine 112 can be turned, for example via a motor 190. A desiccant (also not shown in FIG. 10) can further be provided in the magazine 112, as is also the case in the magazines 112 according to the preceding illustrative embodiments.

Once again, the drum-shaped magazine 112 has two openings 128, 130 in its housing 120. Analogously to the above illustrative embodiments, a closure mechanism 116 is again provided, which has a sealing element 118 with corresponding sealing surfaces 134. The sealing element 118 can be pushed by a drive 136 into the first opening 130, such that a test element 122 is pushed out of the second opening 128 and transferred to the measurement position 138. There, this test element 122 is contacted by the electrical contact 186, and a measurement can be performed. In this position (in contrast to the open position shown in FIG. 10, which is adopted only briefly), the sealing element 118 is driven completely into the openings 128, 130 and closes them. The openings 128, 130 can for this purpose also be equipped with additional seals 132 (which are not shown in FIG. 10). Alternatively or in addition to this, the magazine housing 120, in the area of these openings 128, 130, can also be made of an at least partially deformable plastic into which the sealing element 118 is pressed with a press fit, in order to close the interior of the magazine 112. Alternatively or in addition, as has been described above, the sealing element 118 can also be designed at least partially conical, in order to improve the sealing action. Moreover, analogously to the illustrative embodiment according to FIG. 5 or FIG. 6, the sealing element 118 can also be designed such that it pushes the used test element 122 out of the analysis device 114 after a measurement has been performed in the measurement position 138.

In the embodiment shown in FIG. 10, the magazine 112 can have a comparatively simple design, and all the sealing and/or actuating parts for the individual elements can be assigned to the analysis device 114. Typically, this considerably reduces the costs of the consumer material. Moreover, the overall length of the seal becomes considerably smaller than in the case where the entire magazine shaft 126 were to be sealed off (in which case the loading aperture of the opening mechanism 192 would have to be provided on the analysis device 114 itself), such that the overall force needed upon closure of the opening mechanism 192 after insertion of a new magazine 112 can be considerably reduced. The handling of the analysis device 114 is made easier in this way, and the mechanical structure of the analysis device 114 and of the magazine 112 can be made considerably simpler.

The features disclosed in the above description, the claims and the drawing may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A measurement system comprising an analysis device configured to perform at least one of a measurement function and a sample collection function, the analysis device further comprising at least one replaceable magazine configured to receive at least one consumer element, the magazine comprising a housing having a pair of openings, the magazine being operatively connected to the analysis device, and the analysis device comprising a closure mechanism having at least one sealing element, wherein the sealing element is configured to push at least one consumer element from one of the openings and at least a part of the sealing element comprises a narrowing cross section in a direction of insertion of the sealing element through the one opening, and wherein the sealing element is further configured to sealingly close the magazine when extending through the openings.

2. The measurement system according to claim 1, wherein at least one of the sealing element and the openings are at least partially deformable.

3. The measurement system according to claim 2, wherein the sealing element has a sealing surface, and wherein each opening comprises a seal provided proximal to or within the opening.

4. The measurement system according to claim 1, wherein the sealing element comprises one of a slide and ram.

5. The measurement system according to claim 1, wherein the closure mechanism is configured to convey the consumer element into a measurement or use position by the analysis device by moving the sealing element from a location within the magazine to contact the consumer element to advance the consumer element and at least a portion of the sealing element out of the magazine.

6. The measurement system according to claim 5, wherein the closure mechanism is further configured to convey the consumer element by means of the sealing element from the measurement or use position to one of a disposal position and a disposal unit in the analysis device.

7. The measurement system according to claim 1, wherein the sealing element comprises an elongated jacket movable within the magazine and having at least one external sealing surface for sealing at least opening of the pair of openings when positioned therein and at least one application channel extending axially within the sealing element.

8. The measurement system according to claim 7, further comprising a tip disposed in the application channel, the tip comprising at least one electrical contact configured to provide operative electrical contact between the analysis device and the consumer element, wherein the consumer element comprises an electrochemical test element.

9. The measurement system according to claim 7, wherein an optical device is disposed in the application channel.

10. The measurement system according to claim 7, wherein a mechanical device is disposed in the application channel, the mechanical device comprising a drive ram configured for actuation of the consumer element, wherein the consumer element comprises a lancet system.

11. The measurement system according to claim 1, wherein the consumer element comprises an element selected from the group consisting of a test element, a sample collection element, and a combined consumer element.

12. The measurement system according to claim 11, wherein the consumer element comprises a test element, the test element comprising one of an electrochemical test strip and an optical test strip.

13. The measurement system according to claim 11, wherein the consumer element comprises a sample collection element, the sample collection element comprising a disposable lancet system.

14. The measurement system according to claim 11, wherein the consumer element comprises a combined consumer element, the combined consumer element comprising a combined lancet system and test element.

15. The measurement system according to claim 1, wherein at least a first consumer element is designed as a dummy element.

16. The measurement system according to claim 1, wherein the analysis device comprises a magazine receiver configured to receive the magazine therein.

17. The measurement system according to claim 1, wherein the magazine comprises one of a straight-line magazine and a bar magazine, the magazine further comprising a magazine spring disposed therein and configured to impart a biasing force on a stack of a plurality of the consumer elements provided therein.

18. The measurement system according to claim 1, wherein the magazine comprises a drum magazine.

19. A measurement system comprising an analysis device configured to perform at least one of a measurement function and a sample collection function, the analysis device further comprising at least one replaceable magazine configured to receive at least one consumer element, the magazine comprising a magazine housing, the magazine being operatively connected to the analysis device, and the analysis device comprising a closure mechanism with at least one sealing element, wherein the sealing element has a plunger which is configured to be pushed through a first opening of the magazine to eject the at least one consumer element from at least one second opening of the magazine, and configured such that when the magazine is in a closed state, the sealing element remains in and sealingly closes the first opening and the at least one second opening, and wherein the first opening is larger in size than the at least one second opening.

20. The measuring system of claim 19, wherein at least one of the plunger and at least one of the first and second openings is at least partially deformable.

21. The measuring system of claim 20, wherein the at least one of the plunger and the at least one opening that is at least partially deformable is elastic.

22. The measuring system of claim 20, wherein the plunger has a sealing surface and the at least one opening has a deformable seal element within or adjacent to the at least one opening.

23. The measuring system of claim 19, wherein at least a part of the plunger has a cross-section that narrows in a direction of insertion of the sealing element into the at least one second opening.

24. The measuring system of claim 19, wherein the closure mechanism is configured to convey the consumer element into a measurement or use position by the analysis device by moving the plunger from a location within the magazine to contact the consumer element to advance the consumer element and at least a portion of the plunger out of the magazine.

25. The measuring system of claim 24, wherein the closure mechanism is further configured to convey the consumer element by means of the plunger from the measuring or application position to one of a disposal position and a disposal unit in the analysis device.

26. The measuring system of claim 19, wherein the plunger comprises an elongated jacket movable within the magazine and having at least one external sealing surface for sealing the at least one opening when positioned therein and at least one application channel extending axially within the plunger.

27. The measuring system of claim 26, further comprising a tip disposed in the application channel, the tip comprising at least one electrical contact configured to provide operative electrical contact between the analysis device and the consumer element, wherein the consumer element comprises an electrochemical test element.

28. The measuring system of claim 26, wherein an optical device is disposed in the application channel.

29. The measuring system of claim 26, wherein a mechanical device is disposed in the application channel, the mechanical device comprising a drive ram configured for actuation of the consumer element, wherein the consumer element comprises a lancet system.

30. The measuring system of claim 19, wherein the consumable element comprises an element selected from the group consisting of a test element, a sample collection element, and a combined consumer element.

31. The measurement system according to claim 30, wherein the consumer element comprises a test element, the test element comprising one of an electrochemical test strip and an optical test strip.

32. The measurement system according to claim 30, wherein the consumer element comprises a sample collection element, the sample collection element comprising a disposable lancet system.

33. The measurement system according to claim 30, wherein the consumer element comprises a combined consumer element, the combined consumer element comprising a combined lancet system and test element.

34. The measuring system of claim 19, wherein at least a first consumable element is designed as a dummy element.

35. The measuring system of claim 19, wherein the analysis device comprises a magazine receiver to receive the magazine therein.

36. The measuring system of claim 19, wherein the magazine comprises one of a straight-line magazine and a bar magazine, the magazine further comprising a magazine spring disposed therein configured to impart a biasing force on a stack of a plurality of consumer elements provided in the magazine.

37. The measuring system of claim 19, wherein the magazine comprises a drum magazine.

38. The measuring system of claim 1, wherein the one opening of the pair of openings is smaller than the other of the pair of openings.

* * * * *